United States Patent
Benigno et al.

(10) Patent No.: US 6,230,142 B1
(45) Date of Patent: *May 8, 2001

(54) HEALTH CARE DATA MANIPULATION AND ANALYSIS SYSTEM

(75) Inventors: Benedict B. Benigno; Gerald A. Feuer; Matthew O. Burrell, all of Atlanta; William E. Sadler, Stone Mountain; Leland A. Withers, Atlanta, all of GA (US)

(73) Assignee: Homeopt, LLC, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/139,423

(22) Filed: Aug. 25, 1998

Related U.S. Application Data

(60) Provisional application No. 60/068,825, filed on Dec. 24, 1997, and provisional application No. 60/091,552, filed on Jul. 2, 1998.

(51) Int. Cl.[7] .............................. G06F 17/60; G06F 7/00
(52) U.S. Cl. .................................... 705/3; 705/2; 707/104
(58) Field of Search ............................ 705/2, 3; 707/104

(56) References Cited

U.S. PATENT DOCUMENTS

| | | | |
|---|---|---|---|
| 3,970,996 | * | 7/1976 | Yasaka . |
| 5,277,188 | * | 1/1994 | Selker . |
| 5,361,202 | * | 11/1994 | Doue . |
| 5,517,405 | * | 5/1996 | McAndrew . |
| 5,594,637 | * | 1/1997 | Eisenberg . |
| 5,594,638 | * | 1/1997 | Lliff . |
| 5,724,580 | * | 3/1998 | Levin . |
| 5,732,397 | * | 3/1998 | DeTore et al. . |
| 5,794,208 | * | 8/1998 | Goltra . |
| 5,845,253 | * | 12/1998 | Rensimer et al. . |
| 5,845,255 | * | 12/1998 | Mayaud . |
| 5,867,821 | * | 2/1999 | Ballantyne et al. . |

FOREIGN PATENT DOCUMENTS

WO 9850871 * 11/1998 (WO) .

OTHER PUBLICATIONS

AnHai Doan, Peter Haddaway, and Charles E. Kahn, Decision–Theoretic Refinement Planning: A New Method for Clinical Decision Analysis, Proceeding of the 19th Annual Symposium on Computer Applications in Medical Care (SCAM 95), 1995.*

* cited by examiner

Primary Examiner—Eric W. Stamber
Assistant Examiner—Jennifer I. Harle
(74) Attorney, Agent, or Firm—Needle & Rosenberg, P.C.

(57) ABSTRACT

Systems useful for analyzing data related to clinical pathways and performing actions based upon the analyses. A self-analyzing system for suggesting default clinical pathways for various procedures. A self-analyzing system for suggesting deviation from a current clinical pathway and entry into an alternative clinical pathway based upon historical information about the results of actions. Statistical analysis systems based on clinical pathways. A rating system for care providers or proposed pathways based on historical information. Systems for gathering clinical pathway information. Systems for tracking clinical pathway outcomes based on data collected post-treatment. A system for prequalification for appropriate discharge and post-discharge handling of and communication with a new class of patient, those requiring stable acute care. A questionnaire computer language and subsystem are used in various stages of the systems of the invention. Corresponding methods are also disclosed.

2 Claims, 9 Drawing Sheets

HEALTH CARE DATA MANIPULATION AND ANALYSIS SYSTEM

CROSS-REFERENCE TO RELATED APPLICATIONS

This utility patent application claims the benefit of priority of U.S. Provisional Patent Application, Ser. No. 60/068,825, filed Dec. 24, 1997, and U.S. Provisional Patent Application, Ser. No. 60/091,552, filed Jul. 2, 1998.

BACKGROUND OF THE INVENTION

I. Field of the Invention

The present invention provides data manipulation and analysis systems and methods associated therewith. In particular, the present invention is directed to systems useful for analyzing medical data related to clinical pathways and performing actions based upon the analyses.

II. Background of the Invention

Escalation of medical costs has led to attempts in the past to streamline systems for providing medical care. Attempts to control such costs have heretofore been thwarted by inexact methods of gathering statistical information relevant to the medical care of interest. Certainly, rudimentary systems for tracking patient information have been developed. Moreover, patient treatment information has also been tracked and stored for further analysis. However, to date, there have not been systems for continuously tracking patient information and patient treatment information, such as clinical pathways for the patient, incorporating these into a useful form, and reacting in an automated fashion according to the recorded information. Therefore, consistent with the goal of providing cost-effective medical care, there remains a need for integrated systems capable of tracking and analyzing medical treatment information.

As an example, home health care is expected to account for an ever-increasing amount of medical care to be provided over the coming years. Therefore, cost reduction systems applicable to the home care setting are similarly highly desirable and yet are, heretofore, virtually unknown.

Similarly, there exists a need for effective data tracking and manipulation vital to providing "stable acute" care, as that term is defined and used herein. Historically, patients who had surgery would have to come to the hospital anywhere from one to three days early. After surgery, they would then spend significant time in the hospital and, in years past, these patients would actually be kept in the hospital and on bed rest for a lengthy stay. The operative patient's stay can be broken down to three phases: pre-operative, operative and post-operative. Each of these phases has changed drastically over the years.

During the pre-operative time period, patients historically came to the hospital anywhere from one to three days prior to surgery. Early arrival at the hospital usually was required for patients undergoing abdominal procedures because of the necessary to perform a bowel prep believed to be necessarily done in the hospital. This has changed because patients now can receive an equivalent bowel prep in their own home before coming to the hospital. However, although the bowel prep may be equally effective in cleaning out the intestine, the home prepared patients often become dehydrated. Yet pressures from managed care to save money have forced the medical community to ignore the fact that these patients are often dehydrated.

Additionally, even those patients not needing a bowel prep used to come in one day prior to surgery. A history and physical would be done the night before surgery and then the pre-op, including anesthesia visit and various x-rays and blood tests, would be done prior to the operation. This, too, has changed in that the history and physical is now done in the doctor's office and the pre-op, including the anesthesia visit, laboratories and x-rays, are now done a number of days prior to the operation. Again, the pressures of managed care have reduced the prior one to three day in-hospital pre-operative period to the current practice of admission to the hospital early in the morning of surgery.

Economic pressures have recently forced movement toward minimizing any pre-operative stay. For similar reasons, it would be desirable to minimize post-operative in-hospital stays. One example of the result of this desire is the so-called "drive through mastectomy," which permits discharge from the hospital within 24–36 hours after abdominal hysterectomy or laparoscopic procedures. Unfortunately, in major abdominal procedures, there are great limitations to sending patients home early. These limitations are present for any major procedure requiring an abdominal incision (such as in gynecological oncology, radical hysterectomy, lymph node sampling or debulking, urology, radical prostatectomy, nephrectomy through abdominal approach, general surgical procedures including colectomy, small bowel resection with abdominal approach, or gastrectomy). Once there has been significant manipulation of the intestines after an abdominal incision, there are tremendous limitations to sending the patients home prior to demonstration of gastrointestinal ("GI") function, an event which can easily take four to seven days to occur.

In the operative period, there are many changes that have occurred in the past few years. For instance, the suture materials used today cause much fewer adverse reactions and are much more secure. Staple devices have increased the speed of the operative procedures as well as providing more security resulting in less problems post-operatively. For example, colectomies are now done with staple anastomoses thereby minimizing the likelihood of a leak of stool through the anastomosis is minimal. This, of course, effects the post-operative time period because fewer complications are expected and observed compared to the past. Finally, operative procedures have been significantly refined and improved, which also aids in shorter operating room ("OR") time and less post-op complications.

The post-operative period has seen many changes and improvements over the years, including quicker ambulation of the patient, decreased bed rest, knowledge that faster discharge probably decreases likelihood of venous thrombosis and hospital acquired infections, and understanding that many post-operative situations do not necessitate long hospital stays. For example, patients who had mastectomies used to stay in the hospital for four to five days until the drain stopped yielding fluid. Presently, patients with mastectomies can go home within the first 24 hours of surgery and are taught how to take care of the drains at home. However, there are patients who have had mastectomies who have no care giver at home, yet are expected to take care of the drains, pain, any questions and any emotional discomfort without any assistance. Other improvements include decreased use of nasogastric tube after gastrointestinal procedures including small bowel resection or large bowel resection, use of patient controlled analgesia as opposed to injections which allows the patient to manage his or her pain more easily at home, development of intravenous computerized monitors which prevent against possible IV errors, use of sequential hose which are stockings which blow up on the legs in a sequential manner and significantly decrease the likelihood of thrombosis, use of H2 blockers (Histamine-2 blockers) such as PEPCID®, TAGAMET®, and ZANTAC® in the post-operative setting to significantly decrease the chance of gastric bleeding or other upper GI complications, use of home care for either the chronically ill post-operative patients or the generally chronically ill patient, and the use of improved IV antibiotics to decrease post-operative infections.

Over the past ten to fifteen years, home care has also become a viable option. However, although home care has been quite successful in the past with patients, home care has only been known for handling patients classified as chronically ill or, very recently, for handling patients who would usually come to the emergency room. For a chronically ill patient, the patient remains in the hospital for a long period of time. While it may take 24–48 hours to send the patient home, the stay at home may vary from as much as two weeks to a few months.

Hospital length of stay and other clinical pathways are ultimately the purview of the physician. However, certain guidelines exist, such as those published under the title *Milliman & Robertson Healthcare Management Guidelines* by Milliman & Robertson, Inc., Actuaries & Consultants. These guidelines are gathered manually by physicians and nurses based on their collective judgment of suitable care. The gathering process is tedious and subjective. The resulting "standards" are developed not through the collection and analysis of actual data (such as would be done in preparing, for example, life insurance mortality tables), but instead are developed by committees of clinicians and others who are hired by actuarial companies and asked their subjective opinions. Therefore, these exists a need for an automated system to determine optimal treatment steps so as to improve important factors such as length of post-operative stay and recovery.

For example, the post-operative hospital stay standard for a woman after an abdominal hysterectomy is set today by such a committee. It is referred to as the "optimal" hospital stay for this procedure. If described as a 5-day post-op hospital stay, there are events during the stay that are looked for and flagged, such as a bowel movement. However, there is no data or supporting analysis that concludes that such a woman must remain in the hospital for yet another day if she has not had a bowel movement. It is simply unknown whether a bowel movement truly is a statistically significant variable or event. Rather, in prior art systems, the committee of clinicians, or others, simply make a best guess that this is a significant factor.

Because of economic pressures, it is highly desirable to provide an optimized post-operative discharge program. Additionally, it is highly desirable to provide a system capable of decreasing infection and decreasing the incidence of, for example, venous thrombosis by permitting early discharge.

The post-operative period has changed dramatically over the years from a very lengthy stay only in the hospital to using procedures that allow patients to go home sooner, such as laparoscopically assisted procedures, as well as refining various procedures so as not to require lengthy stays. Again, many of these procedures are procedures that do not require an abdominal incision and yield no problem with post-operative bowel function. In essence, the post-operative stay has already deviated somewhat from the hospital setting to the home.

Using the example of the "drive through mastectomy", the patient has had a complex procedure which may often take up to three or more hours and has suffered a large incision. These patients are nonetheless released from the hospital because the incision is a high one which does not impair their breathing. In addition, because the patient does not have an abdominal incision, there is a low likelihood of any bowel dysfunction. However, a number of problems can still occur. First, the fairly large incision may impart a significant amount of pain for the patient, yet the patient is released with only oral medication while the patient may, in fact, require patient controlled analgesics (e.g., intravenous type medications such as MORPHINE® or DEMERAL®). The patient has also had a very lengthy procedure and depending on the type of anesthesia used, may have some residual anesthesia effects, which could include nausea. The patient may require an IV antiemetic (anti-nausea agents) or intravenous fluids to aid in diminishing the nausea. Many of these patients not only have a long incision with a dressing which could leak or become infected, but they also have one or more drains in place. The patients are instructed in how to use these drains but this can be cumbersome or not entirely understood by the patient.

Moreover, once released, the physician loses track of the patient except for phone calls initiated by the patient to the physician, which may be difficult for many reasons. First, many physician phone calls during the day do not actually reach the physician but rather go to his or her staff. During the evening, the physician may not receive knowledge of the phone call whatsoever and the patient may be forced to go to the emergency room. Therefore, it would be highly desirable to have a system permitting the capability to provide home care and direct information communication to the physician and his or her staff in real time, so as to reduce the recovery period and the risk of complications.

Other patients who are rapidly discharged are post abdominal hysterectomy patients. Often these patients have low transverse incisions which again do not yield significant problems for breathing. However, bowel dysfunction problems may still exist. Patients sometimes have difficulty taking down liquids or food for as many as three or four days. Unfortunately, these patients are sent home after post-op day one to one and a half and, at that time, with current systems, do not have any way of receiving IV fluids in the event they have nausea or difficulty taking in fluids. Additionally, if they have any significant discomfort, they are only on oral medications which may not be potent enough. Therefore, there exists a need for systems and methods for permitting expeditious and appropriate post-operative discharge, while maintaining the capability of providing an appropriate level of care to the patient while the patient continues to recover.

A third example of early discharge includes patients who have had gastrointestinal procedures. Patients with colectomies, after demonstrating the ability to take in fluids without developing abdominal distention, may be discharged from the hospital. These patients remain at risk for developing bowel dysfunction, abdominal distention, and possible major complications such as leakage from a bowel anastomosis. In present day systems, they are nevertheless sent home without any significant continued communication with the doctor or any prearranged skilled nursing care. A tremendous risk exists the patient could become ill and severely dehydrated and require a lengthy stay in the hospital upon re-admission. In some areas of the country, such discharges do not occur because physicians oppose it. There exists a need for a system able to permit such discharged patients to remain safely in the home without the attendant risks described above.

As stated previously, actuarial companies serving the health care industry today do not make recommendations to their customers (e.g., insurance companies, etc.) based upon their analysis of large collections of data as they would in other industries (e.g., life insurance), but instead use subjective, and potentially inaccurate, committees. One reason why this is true might be that actuarial companies simply have not created, nor have access to, the large amounts of data and processes needed to perform such analysis. While others have collected health care data previously, no databases exist whereby the data is organized in such a way so as to enable meaningful analysis of the data, and no processes exist to analyze such data.

The above background describes some pre-existing mechanisms by which patients are released to the home for part of their post-operative period. Each of these mechanisms suffers from drawbacks and is, in some way, not satisfactory in comparison to the use of the present invention as a way to provide appropriate post-operative care to patients, including stable acute patients. The foregoing evidences the significant difficulties and shortcomings of known systems.

SUMMARY OF THE INVENTION

The invention herein solves the drawbacks discussed above. The present invention is directed to data storage and manipulation system whereby clinical pathway data is collected for patients and stored in appropriate databases. The system is, preferably, a client/server based system where clients, such as actuarials, doctors, hospitals, nurses, insurance companies, and other healthcare providers can access a central repository of relevant clinical treatment information. A particularly effective aspect of the invention is that the system includes functionality for continuously reviewing the clinical pathway and treatment data for trends and, where appropriate, prompting appropriate parties of the need to change the default treatment protocols and clinical pathway or to change the particular treatment orders for a patient. While certain trends may be searched for explicitly, an important aspect of the invention is that it continuously reviews the ever-increasing data repository using automatically generated propositions in search of correlations between data elements, even unexpected correlations.

Moreover, the system provides a mechanism for rating proposed clinical pathways. For instance, a caregiver may engage the system to review a proposed pathway against the historical database and the system will provide a ranking, based on the historical data, of the usefulness/effectiveness of the proposed approach in past cases. Moreover, in another aspect of the invention, the rating system is associated with particular care givers, such as doctors or nurses, and their historical performance can be analyzed against the general data set so as to arrive at an objective rating of the caregiver against either given or system generated criteria.

In addition, the system further comprises the functionality of providing follow-up data tracking and analysis. Previous data collection systems are hindered in that, unless there is a complication, data concerning a patient's follow-up status is rarely tracked, and even when tracked, is not tracked in sufficient detail to provide meaningful information. The follow-up data tracking portion of the present invention, however, provides a mechanism for contacting patients and generating additional, clinical pathway related data elements, wherein those elements are incorporated into the analysis for automated analysis of the effectiveness of particular clinical pathways.

For gathering the clinical pathway data, the present invention involves the use of a computerized or electronic system. In the stable acute care scenario, the computerized system is used to address the issue of sending patients home at an appropriate time in the post-operative period. The computer enables appropriate communication between the home, the nurse/caregiver seeing the patient, and the physician or the physician's assistant in the office. This type of care has been heretofore unknown. The system allows providing services to an entirely new class of care, stable acute care.

In one embodiment, the system is used to identify patients who are candidates for early (or late) post-operative discharge (and possibly stable acute care). The nurse or caregiver then sees the patient almost immediately at home and tracks the patient at home one or more times per day using the system and the information is used to create and update the clinical pathway database records for the patient. Real-time communication systems of the invention allow supervision by the physician, while not requiring the supervision to occur in a hospital setting. Assessment of the patient's condition is performed using an questionnaire or form generated based upon the current patient's customized and changeable clinical pathway. In the stable acute care (e.g., "home") setting or facility, the nurse provider can assess the patient and send information regarding the patient by using the questionnaire. The questionnaire itself will create a SOAP (Subjective, Objective, Analysis, Plan) note. The SOAP note is known to those of ordinary skill in the art as the means whereby a physician describes the patient's status and care plan.

Additionally, the system allows the physician or physician's staff to gather historical information regarding the medications, IV fluids, and other therapies provided to a patient and to determine whether or not they were given as ordered. The system also provides the capability to change the orders as needed.

One significant benefit of the invention is that the data gathered about various clinical pathways and their successfulness can be catalogued. The data can be repackaged and manipulated as needed and is believed to be of significant value in and of itself. The gathering of this data as it pertains to the heretofore nonexistent stable acute care patient class is an important advantage of the invention.

The important features of the system of the invention include the use of a computerized or electronic interface between the skilled nurse/caregiver, the patient, and the physician. In addition, the invention relies upon specialized software subsystems that allow the use of the interface, allow immediate translation from questionnaire into on-screen formats which can be read by a physician or staff, and allow prequalifying of patients during the pre-operative period for appropriate (i.e., earlier or later than the average) release and stable acute care.

In prior systems, patients were only sent home when their status had reached the chronic care level. In that case, the loss of a day or two arranging home care was not considered to be a major problem because the chronic care stay at home would last anywhere from two weeks to even four weeks. However, using the present invention, the stay at home is short and once the patient is designated to go home for stable acute care, it is important to proceed with their discharge expeditiously. This rapid process requires the use of systems of the invention which provide for prequalification of patients into the stable acute care program.

Another aspect of the invention is the use of a computerized system for identifying appropriate patients for receiving stable acute care. The system identifies patients who would usually stay in the hospital for a significant period of time because of post-op ileus (delay in bowel function). In addition, the system provides pre-operative training at the doctors office as well as informing the nurse of a patient's imminent discharge so the nurse can meet the patient soon after the discharge into the patient's home.

The communications subsystems of the invention are important to its capability of providing stable acute care and tracking clinical pathways. Point of service communication at home using either a suitable electronic or computerized device is provided by the invention. The computer can be put into communication with a data storage/server computer via any suitable means, including a modem or network adapter.

During stable acute care using the systems of the invention, daily patient visits occur. From two to four visits per day may be required and are contemplated. Daily communication includes SOAP notes, notification of whether the patient received appropriate IV medications and intravenous fluids, as well as the ability to communicate with nurses, and nurse communications with physicians for order changes. The initial orders created when the patient is sent home represent an initial or default clinical pathway anticipating potential problems and providing appropriate care orders at that time.

In addition, using the methods and systems of the present invention, the post-operative patient's stay at home may be as little as from two to five days. In order not to lose a day or two days of potential early discharge, the patient is preferably identified and classified as an early discharge candidate prior to hospital admission.

The present invention provides systems and methods with numerous advantages. One such advantage provided by the system is the emotional advantage of sending the patient home in his or her own environment at the appropriate time, as soon as practicable under the new system. Such patients will often be more comfortable, in a psycho-social sense, and many of the difficulties that occur in the hospital regarding nursing care not being accessible are removed. A patient having a 24-hour a day caregiver directed specifically to him or her eliminates most difficulties with regard to immediate appropriate care, i.e., care that does not involve skilled nursing care such as turning on IV pumps, changing an IV bag, or working with IV medicines. In addition, skilled nursing care visits vary anywhere between two and four times a day (or whatever frequency and level of care is necessary) and amount to less burden than what is required from nurses in the hospital setting.

Another aspect of the invention involves a new questionnaire format, which may be used as one way of collecting the data to be analyzed according to the present invention. This questionnaire format allows stable acute care caregivers the ability to closely track and instantly inform a patient's physician of that patient's condition. The format, as it applies to a particular patient, also provides the clinical pathway for the patient, as described infra. With the present invention, stable acute care providers receive updated orders about the patient on a visit by visit basis and physicians are able to track the progress of their patients instantly. The questionnaire system in conjunction with the other components of the systems of the invention allows the close communication required between home care givers and physicians in this kind of situation and solves various problems of the prior art. Statements of the language used to create each questionnaire are saved in the clinical pathway database as opposed to a simple flat file. Entire questionnaires are versioned, and may be easily modified, or recalled from earlier versions. Questions once entered may be reused in many questionnaires.

In one embodiment, the invention provides a system for manipulation and analysis of data related to clinical pathways, comprising a clinical pathway database for storing an initial procedure decision data element, corresponding to a decision point within the clinical pathway and at least one, preferably a plurality of, subsequent decision data elements, corresponding to available subsequent decision points within the clinical pathway, a historical clinical pathway database for storing previously selected subsequent decision data elements, selected corresponding to the initial procedure decision data element, processing means, including a storage device, for performing the steps of selecting one of the at least one subsequent decision data elements, comparing the selected subsequent decision data element with the previously selected subsequent decision data elements stored in the historical clinical pathway database, and based upon predetermined correlation criteria, modifying the subsequent decision data elements within the clinical pathway database.

In addition, the present invention provides a client/server system for manipulation and analysis of data related to clinical pathways, comprising a communication network, a client workstation in communication with the communication network, wherein the client workstation comprises means for generating at least one signal corresponding to a clinical pathway decision and transmitting the at least one decision signal over the communication network, and means for receiving at least one signal corresponding to a clinical pathway modification from the communication network, and means for outputting the at least one modification signal to a signal processing means, a server on the communication network, wherein the server comprises a clinical pathway database for storing an initial procedure decision data element, corresponding to a decision point within the clinical pathway, and at least one subsequent decision data element corresponding to at least one available subsequent decision point within the clinical pathway, and a historical clinical pathway database for storing previously selected subsequent decision data elements, selected corresponding to the initial procedure decision data element, and processing means, in communication with the communication network, the client workstation, and the server, for performing the steps of receiving the at least one decision signal from the communication network, based on the received decision signal, selecting one of the at least one subsequent decision data elements, comparing the selected subsequent decision data element with the previously selected subsequent decision data elements stored in the historical clinical pathway database, and based upon predetermined correlation criteria, modifying the at least one subsequent decision data elements within the clinical pathway database, then generating at least one signal corresponding to a clinical pathway modification of the subsequent decision data elements in the clinical pathway database, and transmitting the at least one clinical pathway modification signal over the communication network to the receiving means of the client workstation.

The present invention also provides a system for manipulation and analysis of data related to clinical pathways, comprising a clinical pathway database for storing an initial procedure decision data element, corresponding to a decision point within the clinical pathway, and at least one subsequent decision data element corresponding to at least one available subsequent decision points within the clinical pathway, a historical clinical pathway database for storing previously selected subsequent decision data elements, selected corresponding to the initial procedure decision data element, and processing means, including a storage device, for performing the steps of selecting one of the at least one subsequent decision data elements, comparing the selected subsequent decision data element with the previously selected subsequent decision data elements stored in the historical clinical pathway database, and based upon predetermined correlation criteria, modifying the at least one subsequent decision data element within the clinical pathway database.

In a further embodiment, the present invention provides a system for assessing utilization of medical resources based upon manipulation and analysis of statistical data related to clinical pathways, comprising a clinical pathway database for storing an initial procedure decision data element, corresponding to a decision point within the clinical pathway, and at least one subsequent decision data element corresponding to available subsequent decision points within the clinical pathway, a historical clinical pathway database for storing previously selected subsequent decision data elements, selected corresponding to the initial procedure decision data element, and, for each of the previously selected subsequent decision data elements, a utilization value corresponding to the decision data element processing means, including a storage device, for performing the steps of selecting one of the at least one subsequent decision data elements, comparing the selected subsequent decision data element with the previously selected subsequent decision data elements stored in the historical clinical pathway database, and based upon predetermined correlation criteria, modifying the at least one subsequent decision data elements within the clinical pathway database, and statistical processing means, in communication with the clinical pathway database and the historical clinical pathway database, for performing the steps of accessing the historical clinical pathway database, computing pathway utilization value based on the accessed utilization values in the database, generating at least one signal corresponding to the pathway utilization value, and outputting the at least one utilization value signal to a signal processing means.

In another embodiment, the invention provides a system for rating medical care based upon manipulation and analysis of data related to clinical pathways, comprising a clinical pathway database for storing an initial procedure decision data element, corresponding to a decision point within the clinical pathway, and at least one subsequent decision data element corresponding to available subsequent decision points within the clinical pathway, a historical clinical pathway database for storing previously selected subsequent decision data elements, selected corresponding to the initial procedure decision data element, and, for each of the previously selected subsequent decision data elements, a rating value, processing means, including a storage device, for performing the steps of selecting one of the subsequent decision data elements, comparing the selected subsequent decision data element with the previously selected subsequent decision data elements stored in the historical clinical pathway database, based upon predetermined correlation criteria, modifying the subsequent decision data elements within the clinical pathway database, and statistical processing means, in communication with the clinical pathway database and the historical clinical pathway database, for performing the steps of accessing the historical clinical pathway database, computing a pathway rating value based on the accessed rating values in the historical database, generating at least one signal corresponding to the pathway rating value, and outputting the at least one rating signal to a signal processing means.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

Figure 1A:
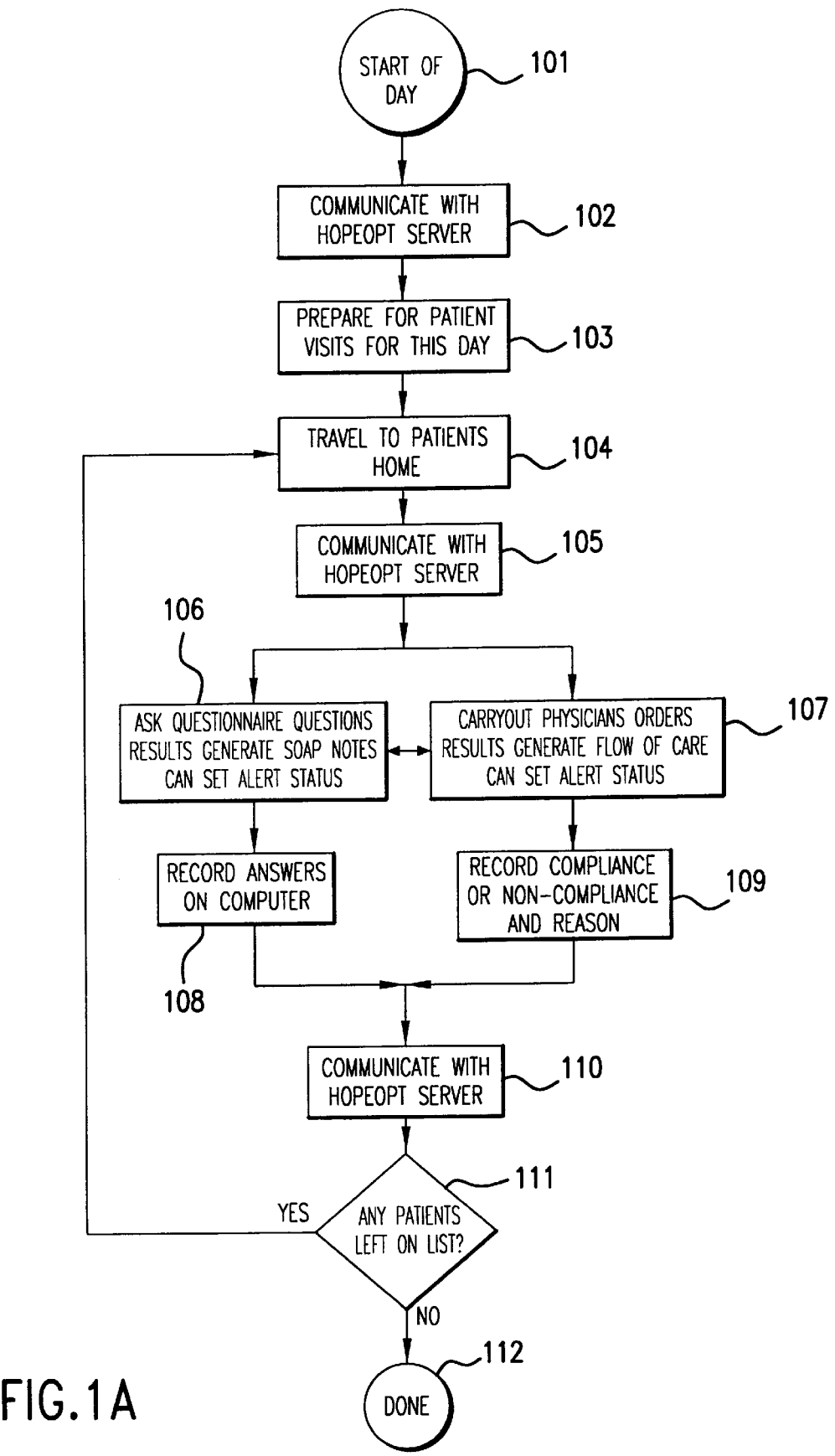
FIGS. 1A and 1B show flowcharts of the questionnaire system in operation from the care giver's point of view.

The present invention may be understood more readily by reference to the following detailed description of preferred embodiments of the invention.

Before the present methods and apparatuses are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

The present invention provides a wide range of systems and processes for automating and improving upon the collection of clinical data, and the actuarial and statistical analysis of that data. In one embodiment, these systems and techniques can be applied to the health care industry, but may also have other applications as well.

In one embodiment, the present invention provides a "feedback loop" where automated actuarial analysis of an ever-growing collection of data provides ever-improving suggestions to a physician or other decision-making authority. These suggestions may take the form of recommendations of changes to continuously improve clinical pathways (as will be defined in further detail below). These suggestions can occur because the automated system of the present invention may search for statistically significant variables and correlations within the collected body of data, and the present invention may thereafter make suggestions or actually alter the existing clinical pathways based upon its analysis of the data.

As used herein "stable acute care" refers to the level of care that would, in the past, have required administration of the care in a hospital setting. Thus, stable acute care refers to care which would have been acute care in the hospital setting and which, when not in the hospital setting, is above the level of care of chronic home care.

As used herein, the term "clinical pathway" refers to a decision tree corresponding to the care of a patient. The decision tree that is the clinical pathway can have one or more nodes and each of these nodes can have one or more links to additional nodes in the tree. Each node can correspond to a care decision and can include additional information about the care actually given. The traversal of the tree, through each decision node, to the next node in the tree represents the clinical pathway. The end effect of the clinical pathway is to document the step-by-step treatment of the patient.

I. Data Manipulation and Analysis System

The present invention provides a system for (and corresponding methods for) manipulation and analysis of data related to clinical pathways. The system includes a clinical pathway database. In one embodiment of the present invention, clinical pathway database models a decision tree comprising various decision nodes. These nodes are stored as either text or tokenized representations of the Questionnaire Language ("QL") statements (see infra). The records can have the following structure:

Protocol ID

Group ID

Question ID

Version

Ordinality

Question Text

The protocol ID is the protocol being defined. Group ID identifies the grouping of the question with like questions, i.e., all related questions belong to the same group, and are displayed in a single group box on the screen. Question ID is the identifier of the question itself. Version is the version of the question being asked. Ordinality is the order of the question within its group. Finally, the question text is the QL statement itself.

As each patient is added to the system, a copy of the base questionnaire for their procedure is produced and offered to the physician or system operator for change. The base questionnaire is simply a set of the clinical pathway node structures as described above. As individual questions are changed, they are versioned, e.g., by incrementing a version number. Versioning of the question can also include further information, such as date and time of the change, identity of the party making the change, original question text, etc., such that the system can provide a suitable audit trail to review all changes in any particular questionnaire.

In accordance with the present invention, the database stores an initial procedure decision data element (using the structure set forth above) corresponding to a decision point within the clinical pathway and at least one, preferably a plurality of, subsequent decision data elements, corresponding to available subsequent decision points within the clinical pathway. The system also includes a historical clinical pathway database for storing previously selected subsequent decision data elements, selected corresponding to the initial procedure decision data element. In addition, the system includes a processing means, optionally including a storage device, for various steps. While the present invention has been described in terms of particular data structures and data flow, the computational steps could be carried out by any Von Neuman machine, i.e., the processing means can be any programmable digital computer, whether imbedded into a device or not or whether part of a network or not.

Also, in accordance with the present invention, the present invention provides methods for determining the quality of a clinical pathway. For instance, in one such method a default pathway is determined by, e.g., experts in the field or by the administrator of the present system. This default clinical pathway is flagged in the database as a default pathway. Using the systems described elsewhere herein, data is collected on the decisions taken and care given along the actual clinical pathway. The system further records any deviations from the default pathway by users of the system. This data is then used for the feedback systems of the present invention.

In one embodiment, the feedback system tests correlations against sets of criteria and question results. The criteria can be generated by the system administrator or user or can be generated after analyzing data in the system. For example, the system can be pre-configured to track costs, hospital stays, and long term complications. In this configuration, for each decision point made within the clinical pathway and for each patient, the database records a particular result. In addition, the system also records the path taken through the decision tree (clinical pathway) and this path is then correlated against the result variables of interest to determine if there is any correlation. For example, the decision as to whether or not to prescreen (by asking a background question using the QL) for diabetes may alter the final cost and/or hospital duration for a particular patient. Therefore, depending upon the magnitude of these influences, a correlation can be determined to exist or not.

As noted above, a predefined preliminary set of these correlation searches may be entered manually and the system is configured to search this problem space automatically. The correlation matrix potentially includes all combinations of all questions in the questionnaire versus all recorded outcomes. Selecting and matching significant independent variables which result from this problem space is computationally NP-complete. However, one of ordinary skill in the art would recognize a number of suitable correlation algorithms useful for finding plausible solutions to this NP-complete problem space. As one example, and not intending to be bound to any particular implementation, the selection and matching of variables can be carried out using genetic programming or genetic algorithm ("GA") methods. Such algorithms can generate hypotheses upon which to test correlations. As used for the present invention, a GA will search the set of questionnaire decision points and correlate decisions against the various output variables. The system is constantly evaluating itself. As the system finds new correlating factors, they are put in place to aid in determining changes to be made to the current or default clinical pathway. In addition, as correlations are determined between clinical pathway decisions and significant outcomes (i.e., outcomes of interest), changes can be made to the default pathway to optimize systematically the clinical pathway toward the desired results. These changes can be automatically made or can be presented to the physician, system administrator, or other user for approval.

In addition to GAs, there are other suitable methods for attacking the present NP-complete problem. For instance, correlations can be viewed as patterns and the patterns then subjected to pattern matching routines. Such pattern matching is a known domain of neural networks. However, even if neural networks are used, it is preferred that the nodes and loadings still be determined by a GA. GAs can also be used in this manner to actually create analysis programs by determining an input grid for a finite state machine. Other methods for finding near optimal solutions for NP-complete problems could also be used to determine the optimal correlation matrix, such as simulated annealing. No matter the approach, one of skill in the art would recognize that the present correlation problem is combinatorily explosive is likely impossible to be attacked at all with closed form or brute-force methods.

The above-described problem is a multivariate analysis where the independent variables are the answers to questions asked during the treatment of the patient. Dependent variables are the desired outcomes. The data space is well defined, with definite sets of potential independent variables and definite sets of potential dependent variables. Difficulty exists however because the data set is so large, and which variables are significant is not known.

Traditionally this problem has gone unsolved by machine methods. The typical solution is to have domain experts determine what they believe are the significant independent variables and measure correlation to effect on desired dependent variables using standard multivariate analysis techniques. While this can lead to advances (indeed, all advances to date are done this way) there is no way to find the hidden dependencies which exist in the data sets.

Again, the selection of the possible sets of independent variables for each dependent variable is an NP complete problem, and is considered to be computationally intractable. However, while there are no definite solutions to NP complete problems, it is possible to find multiple local maxima and minima, and to progressively move towards more optimal solutions.

As described in further detail elsewhere, the specific application of the techniques comprising the present invention is, in one embodiment, for a treatment decision tree for a particular ailment. The decision tree is determined by a clinician. This tree is recorded in a computer database as a series of questions, which are asked to patients and their caregivers. Data is collected in much greater detail about each step of the treatment process than has ever been done before. Time based information is also collected. This gives not only the treatment, but also the exact sequence of events for the treatment.

The questionnaire and its answers are all stored. As the store becomes large, they may be analyzed for variance in treatment leading to more desired results (long term efficacy, reduced cost, etc.). The method for analysis chosen is a Genetic Algorithm (GA).

The mathematics of the Genetic Algorithm are based upon the study of complex non-linear systems. This field has come to be known as "Complexity Theory". Complexity theory discusses the phenomenon of "emergent systems"—systems that are defined by very simple rules, but which exhibit extremely complex behavior because of the non-linear nature of the problem. Complexity theory itself arose out of the study of non-linear dynamical systems in a field, which has been called "chaos theory". There are several excellent references to these fields, including: "Chaos and Fractals, New Frontiers of Science" by Peitgen; "Applied Chaos Theory, A Paradigm for Complexity" by Cambel; "Complexity, Metaphors, Models, and Reality" by Cowan, among others.

Genetic programming has significant advantages over previous attacks on NP complete problems, yielding order(s) of magnitude faster convergence to local minima, with the added bonus that the system does not tend to settle on local minima but to continue to search the phase space of the problem for different solutions. Results of typical GA performance can be found in "Genetic Programming" and "Genetic Programming II" by Koza.

We begin by defining some terms:

Genotype—a string representation of the parameters that will define a solution to a particular problem. In this case, it is a representation of a Clinical Pathway along with its potential answers, which amounts to a single individual in the population of potential solutions.

Fitness Function—a method for evaluating genotypes against some criteria set for which the population is being optimized.

Mutation—random changes performed to the Genotype.

Population—a collection of genotypes.

Reproduction—the creation of new individuals by recombining the individual genes of different genotypes.

The problem of optimizing the performance of a clinical pathway versus different criteria has several unique features among genetic algorithms.

First, the exact set of criteria for which the pathway can be optimized is not known. This means that the fitness function has to be dynamic, as opposed to static as in standard GA approaches. The very dynamic nature of the fitness function suggests a two tiered GA approach to the solution. Not only are populations tested against specific criteria, they are tested against different criteria. The optimization not only looks at input data, but input data along with different fitness functions. The purpose is to search for existing but unsuspected correlations.

In a standard GA, the fitness function is fixed. Therefore, the system can only optimize towards those fixed criteria. In this system, not only can the subset of input (independent variables) be searched, but the subset of criteria (dependent variables) can also be searched. This leads to a problem of representation: How is a genotype represented? One approach used in the present invention is as follows, as also described elsewhere:

Clinical pathways are stored as a series of questions. Each question can be thought of as a decision point within a decision tree, and each question is uniquely identified. Data is collected from the patient at each point within the decision tree that represents the care given that patient. Also, medical history is collected in the same way, as answers to pre-defined questions. Lastly, result information is collected in the same manner. This yields a huge phase space for the algorithm to search. The data must be represented in a manner such that simple manipulation of a string will yield results.

The representation chosen is one that consists of a string that represents the answers to questions. For example, if questions 1, 2 and 3 had possible answers of Y/N, A/B/C, D/E/F the genome would consist of 3 packets of information, the actual string (for instance YAD) and constraining information (Y/N, A/B/C, D/E/F). The string can then be mutated by random selection from available answers. This prevents mutation from producing meaningless answers.

This approach has an analog in genetics, where genes are constructed of simple proteins. Mutation can only select between the proteins to produce a new gene. The concepts are identical.

Note that dependent variables are represented in the same manner. The point of the search then is to find subsets of the problem data space that reflect a causal relationship to other subsets within the data space. Also note that this is a substantial departure from how traditional GAs are performed—the fitness function is also represented in this manner. Questions that would be asked for fitness, i.e.

Variable A>value Y, can also be represented in the same manner. In this case, the question would be a 3 part string, where the first part is the list of possible variables, the second is a list of possible logical operators, the third is another list of possible variables. This allows the fitness function to be manipulated by the GA as well.

A summary of the differences between standard GAs and the present approach is provided below:

1) Dependent and independent variables are represented together in a single data space.
2) Fitness functions are represented within the same data space.
3) The object is to locate causal effects within the entire data space, as opposed to a narrowly defined fitness function.
4) There is no terminal condition that signals the end of the GA. The process continues indefinitely.

Figure 5:
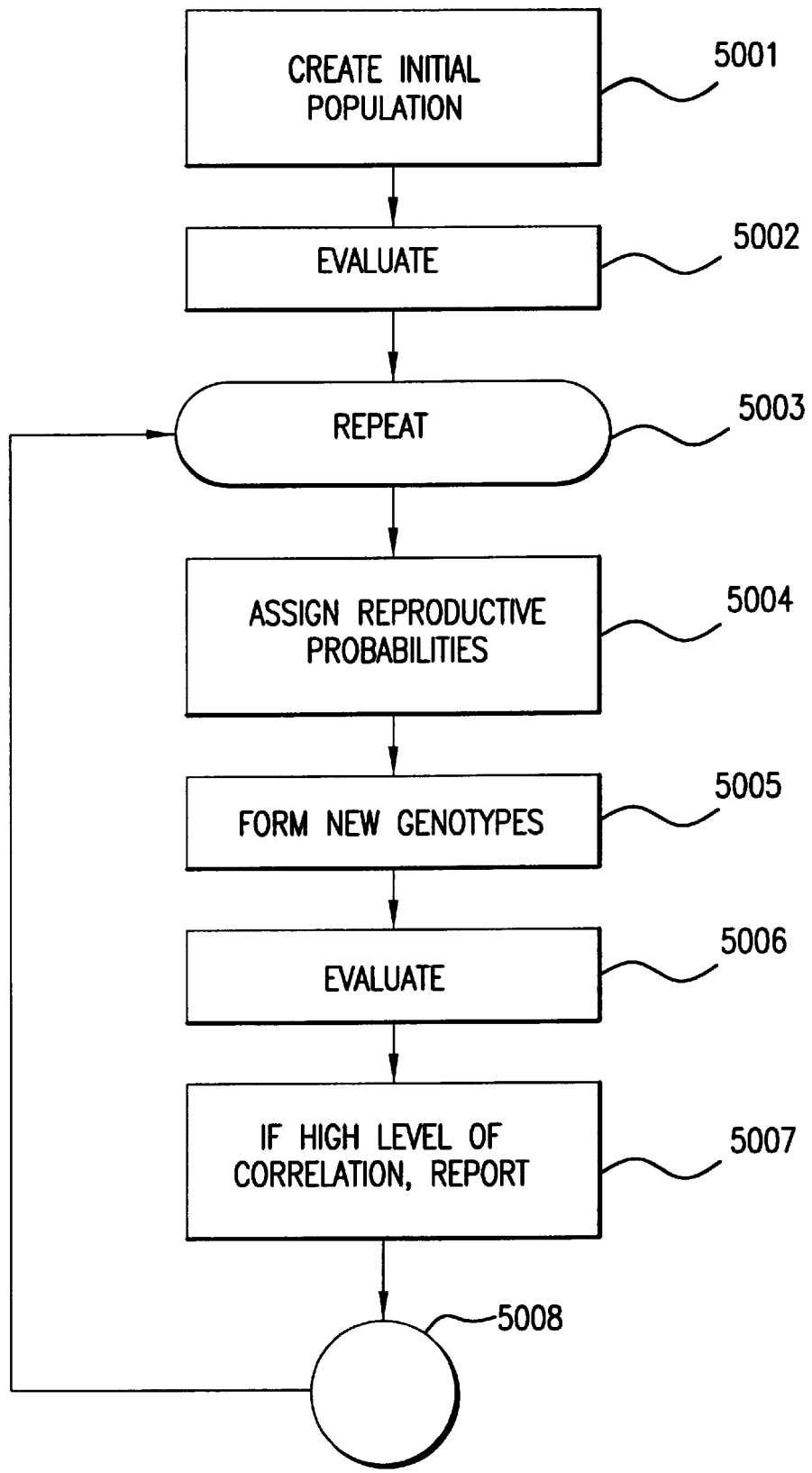
FIG. 5 shows a flowchart of a genetic algorithm analysis process, which may be used in one embodiment of the present invention.

For this specific problem, the following methodology may be followed, described with respect to FIG. 5. For purposes of the process described below, the reference numerals in [brackets] correspond to like-numbered reference numerals shown in the figure:

[5001] Create initial population—the population will initially be determined by "best guess" from human clinicians, along with the sets of independent, dependent, and fitness variables.
[5002] Initial population is evaluated.
[5003] Repeat the following steps:
[5004] Assign reproductive probabilities based upon individuals fitness
[5005] Form new genotypes with recombination and mutation
[5006] Evaluate the new population.
[5007] If high level of correlation is found report it.
[5008] Go to step 5003

There are several exceptions to the routine that must be allowed. For instance, there may be factors that are always optimized. Cost would be a good example. If lower costs are desired, then those genes that define the fitness function that evaluate cost can be marked as being permanent. They will always be in the fitness function. This would be entered as "delta cost less than 0".

The second exception to the fitness rules are weighing. Fitness statements are simply taken as a point score on the basis of the number of true statements. For instance, if there are 10 fitness statements, if all 10 are true, then the genotype scores a 10. It is possible to weigh a statement. If there were a fitness statement that you wanted to defiantly select against, assign it a weight of negative infinity. An example of this would be increased mortality. The fitness statement, "delta mortality greater than 0" would be weighed as negative infinity, then if that case were true (mortality is higher) it wouldn't matter what the other fitness function values were, the genotype would be selected against.

As noted above, the data elements can represent a default clinical pathway and, thus, the system updates the default pathway to be presented to users in the future. Alternatively, the pathway can be the one currently being followed, where some input generates a correlation that causes a deviation or modification (or suggestion to take one) to the pathway.

In a further embodiment, the system includes means for storing the selected subsequent decision data element in the storage device. Suitable storage devices include diskettes, random access memory, or any other device capable of storing digital information.

In an enhanced version of the system, the clinical pathways in the database are each associated with a particular medical procedure. This can be done by offering a new database, or extending the clinical pathway database further to include a medical procedure data element corresponding to the initial and subsequent decision data elements for a particular medical procedure. As is evident, the system is readily suited and optimal for tracking care which can be classified as stable acute care as that term is used herein.

In another embodiment, the processing means further comprises means for, prior to modifying the subsequent decision data elements within the clinical pathway database, querying the user for authorization to make the modification. For instance, if the user is at a computer terminal, a prompt can be given to the user describing the correlation that was found and requesting authorization to, e.g., change the default clinical pathway presented to other users. Assuming the user is trusted or has valid access, the change can be made globally on behalf of all users of the system.

In a further embodiment, at least one of the subsequent decision data elements corresponds to an appropriate discharge of a patient. In this system, the processing means also includes means for comparing the selected subsequent decision data element with predetermined appropriate discharge criteria and, based upon the comparison, generating a signal corresponding to the appropriateness of discharging the patient. Such comparing means can be implemented, for example, using computer software in conjunction with the above described system. The signal can correspond to various states, including permissibility/advisability of discharge or lack thereof.

In another embodiment, the historical clinical pathway database further comprises a medical procedure data element corresponding to the initial and subsequent decision data elements for a particular medical procedure and wherein the processing means further comprises means for storing the medical procedure data element. In this system, the modified subsequent decision data elements are also stored within the historical clinical pathway database. The system includes means for correlating the modified subsequent decision data elements in the historical clinical pathway database with the medical procedure data element, means for querying the historical clinical pathway database and generating a signal corresponding to the subsequent decision data elements corresponding to a particular medical procedure, and means for outputting the signal to a signal processing means. Suitable signal processing means include, a communication network, a computer, a storage medium, a display, a printer, or the like.

In another embodiment, the clinical pathway database further comprises a patient identification data element corresponding to the initial and subsequent decision data elements for a particular patient. In this fashion, the clinical pathways can be associated with particular patients. The identification element can identify the patient directly, or can be an anonymous or random identifier if patient confidence is critical or desired.

In another embodiment, the clinical pathway database further comprises at least one patient visit data element corresponding or related to the patient identification data element. For settings such as stable acute care or home care, the clinical pathway events are generally in terms of "visits." Therefore, in this embodiment, the system allows correlations based upon patient visits and this data element becomes a part of the overall feedback system. In yet another embodiment, the clinical pathway database further comprises a time stamp data element corresponding to each of the at least one patient visit data elements, and the processing means further includes means for comparing the time stamp data element to predetermined criteria, and means for generating a signal corresponding to the result of the comparison and outputting the signal to a signal processing means. Thus, the system allows correlations based upon the visit duration (one example of a predetermined criteria generally of interest) or chronology.

In a further embodiment, the system includes a database for storing follow-up information and wherein the comparing means of the processing means is further responsive to the stored follow-up information in the follow-up information database. Where available, follow-up visit information is incorporated into the databases of the system and the system can use the follow-up information to determine correlations. For instance, if the patient's condition deteriorates months after the procedure, a correlation might be found in some treatment activity in the original clinical pathway. In essence, the pathway is continued forward an indefinite amount of time tracking the patient.

Figure 4:
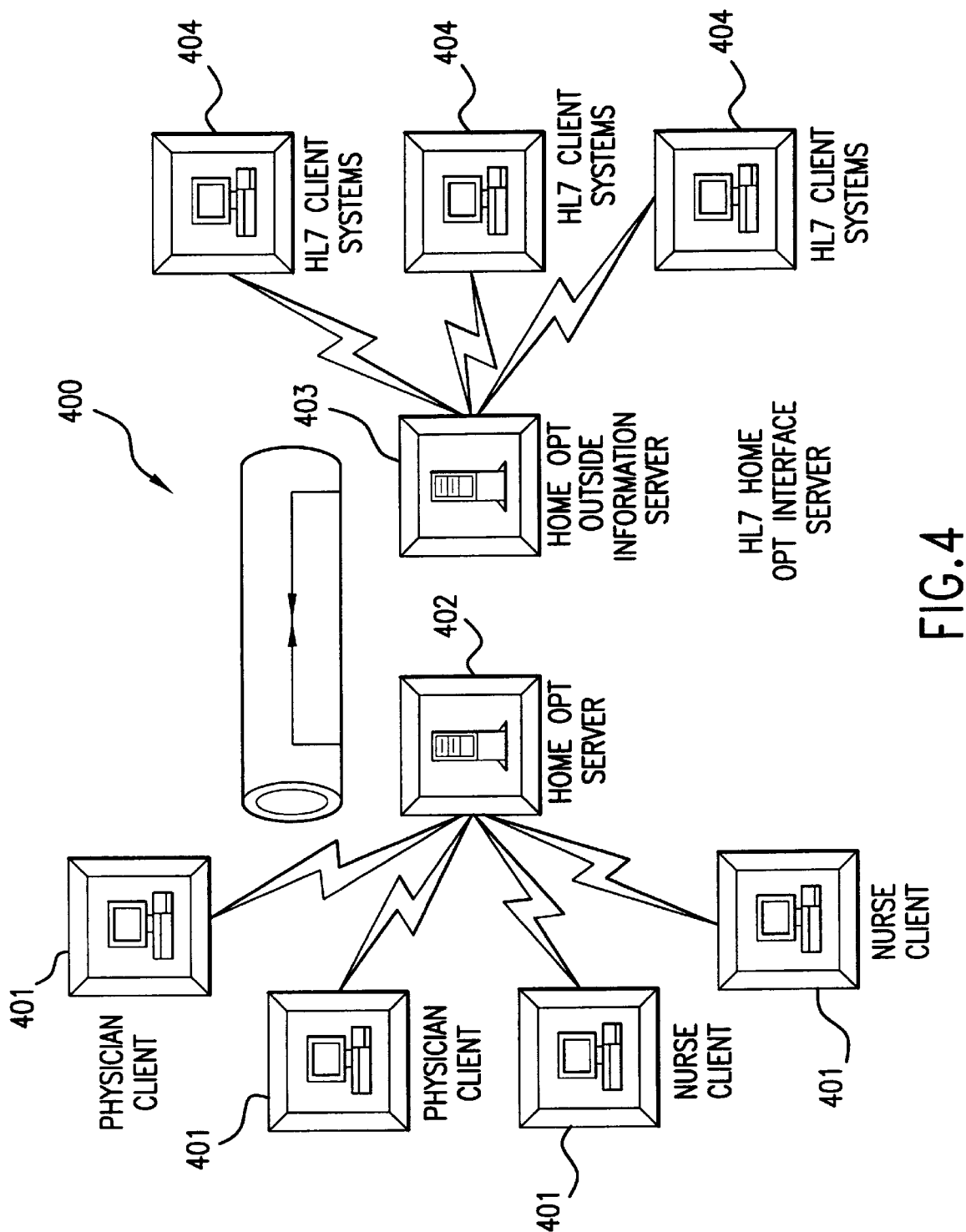
FIG. 4 shows a block diagram of a client/server embodiment of the system of the invention.

In addition, in one embodiment, the present invention provides a client/server system for manipulation and analysis of data related to clinical pathways. Referring now to FIG. 4, one possible client/server configuration 400 useful for practicing the present invention is shown. The system accommodates an arbitrary number of physician or nurse clients 401. A major portion of the communication system of the invention is used to handle connections by physicians and nurses to the system. In one embodiment, data is converted internally to a more efficient format than the external standard HL7 protocol. All communications are coordinated by the server 402 of the system. When a physician or nurse requests information from a source 404 outside of the system, the information may be retrieved from an outside information server 403. Of course, both servers 402, 403 could be implemented on a single machine, if desired. The outside information server 403 contains a translation mechanism for handling translation to and from internal representations based on HL7. By interfacing with HL7, the system of the invention is capable of accessing patient information from existing HL7 external clients 404, as well as serving such information to HL7 systems requesting it.

Thus, the client/server system includes a communication network. In addition, the system includes at least one client workstation in communication with the communication network, where the client includes means (such as a modem or network adapter) for generating at least one signal corresponding to a clinical pathway decision and transmitting the at least one decision signal over the communication network. In addition, the client includes means (which can also be a modem or network adapter) for receiving at least one signal corresponding to a clinical pathway modification from the communication network. The client further includes means for outputting the at least one modification signal to a signal processing means (such as a monitor, printer, digital storage device, network connection, or further computing system). The system also includes a server on the communication network and the server includes (locally or remotely via appropriate connectivity) the clinical pathway database for storing an initial procedure decision data element corresponding to a decision point within the clinical pathway and at least one subsequent decision data element corresponding to available subsequent decision points within the clinical pathway. In addition, also associated with the server is a historical clinical pathway database (the two databases could, of course, exist on a single machine and, in fact, could have overlapping storage) for storing previously selected subsequent decision data elements, selected corresponding to the initial procedure decision data element. Finally, the system includes processing means, in communication with the communication network, the client workstation, and the server, for performing various steps. The processing means is responsible for receiving the decision signal from the communication network and, based on the received decision signal, selecting one of the subsequent decision data elements. Then the processing means is responsible for comparing the selected subsequent decision data element with the previously selected subsequent decision data elements stored in the historical clinical pathway database, and, based upon predetermined correlation criteria, modifying the subsequent decision data elements within the clinical pathway database. Finally, the processing means is responsible for generating at least one signal corresponding to a clinical pathway modification of the subsequent decision data elements in the clinical pathway database and transmitting the at least one clinical pathway modification signal over the communication network to the receiving means of the client workstation.

The present invention also provides a system for manipulation and analysis of data related to clinical pathways, comprising a clinical pathway database for storing an initial procedure decision data element corresponding to a decision point within the clinical pathway, and at least one subsequent decision data element corresponding to available subsequent decision points within the clinical pathway, a historical clinical pathway database for storing previously selected subsequent decision data elements, selected corresponding to the initial procedure decision data element, and processing means, including a storage device, for performing the steps of selecting one of the subsequent decision data elements, comparing the selected subsequent decision data element with the previously selected subsequent decision data elements stored in the historical clinical pathway database, and based upon predetermined correlation criteria, modifying the subsequent decision data elements within the clinical pathway database.

In a further embodiment, the present invention provides a system for assessing utilization of medical resources based upon manipulation and analysis of statistical data related to clinical pathways, comprising a clinical pathway database for storing an initial procedure decision data element corresponding to a decision point within the clinical pathway, and at least one subsequent decision data element corresponding to available subsequent decision points within the clinical pathway. The system also includes a historical clinical pathway database for storing previously selected subsequent decision data elements selected corresponding to the initial procedure decision data element, and, for each of the previously selected subsequent decision data elements, a utilization value corresponding to the decision data element. The system also includes processing means, optionally including a storage device, for selecting one of the subsequent decision data elements and comparing the selected subsequent decision data element with the previously selected subsequent decision data elements stored in the historical clinical pathway database. Based upon predetermined correlation criteria, the system then modifies the subsequent decision data elements within the clinical pathway database. In addition, the system includes a statistical processing means, in communication with the clinical pathway database and the historical clinical pathway database, for accessing the historical clinical pathway database, computing a pathway utilization value based on the accessed utilization values in the database, generating at least one signal corresponding to the pathway utilization value, and outputting the at least one utilization value signal to a signal processing means.

In an alternate embodiment, the system for determining optimal pathways is responsive to criteria determined to assess efficacy of the pathway. For instance, if the system is configured to optimize for three variables, e.g., minimization of cost, time of stay, and post-op complications, then clinical pathways are simply ranked according to their overall efficacy under the stated criteria. Any clinical pathway that departs from a clinical pathway already resident in the database of the system can be annotated as being untested relative to the criteria. As patient information is accumulated about the new criteria, it is evaluated along with all the other criteria already resident in the system. Because the system coordinates communications between a physician and attending nurse, in each case the information needed to track a clinical pathway's progress must necessarily pass through the system at which time the system can record and then or later analyze the path. The system is then able to determine all known pathways used to treat a particular problem and this data set can form one statistical database into which queries are made to determine efficacy.

The selection of criteria on which to base rankings may be entered along with the weightings of the criteria. For instance, using the three criteria above, these criteria can be manually ranked in the following order: least complications, shorter stay, lower cost. Any pathway which results in a higher incidence of complications will be ranked below any which have lower rates, even if they have lower cost because cost is not the primary criteria. In addition, the system itself can suggest ranking order, rather than relying on manual entry in all cases.

In addition, using the present system, as described above, it is possible to assign weights to the rankings as opposed to making them simple absolute rankings relative to each other. In this embodiment, it would be readily be possible for a weighted combination of least cost in conjunction with shorter stay to outweigh differences in complications.

In another embodiment, the invention provides a system for rating medical care based upon manipulation and analysis of data related to clinical pathways, including a clinical pathway database for storing an initial procedure decision data element, corresponding to a decision point within the clinical pathway, and at least one subsequent decision data elements corresponding to available subsequent decision points within the clinical pathway. The system also includes a historical clinical pathway database for storing previously selected subsequent decision data elements, selected corresponding to the initial procedure decision data element, and, for each of the previously selected subsequent decision data elements, a rating value. In addition, the system includes processing means, including optionally a storage device, for selecting one of the subsequent decision data elements, comparing the selected subsequent decision data element with the previously selected subsequent decision data elements stored in the historical clinical pathway database, and, based upon predetermined correlation criteria, modifying the subsequent decision data elements within the clinical pathway database. The system further includes statistical processing means, in communication with the clinical pathway database and the historical clinical pathway database, for accessing the historical clinical pathway database, computing a pathway rating value based on the accessed rating values in the historical database, generating at least one signal corresponding to the pathway rating value, and outputting the at least one rating signal to a signal processing means.

With the present invention, the clinical pathway database of the system can, in one embodiment, be initialized with current proposed optimal clinical pathways. As a physician makes changes in the default pathway, a departure index is be created that is a measure of how far from the original pathway the physician is. In one embodiment, this index is calculated as a simple geometric distance from the current pathway. In such an embodiment, clinical pathways and their associated decision tree nodes are represented as points in n-space, thus making a distance function easy to compute. N-tuple representations of a particular clinical pathway decision tree also provide an exact identifier for that tree. No evaluation of the efficacy of the pathway can be made unless the particular departure is one that is already known to the system. Likewise, if a pathway is too different from existing pathways, then the system is configured to circumvent evaluations at all, even distance calculations, because the pathway is, in fact, in a different arbitrary space. In this case, new data for that clinical pathway decision tree is determined incrementally as new statistical data for the decision tree is collected over time.

For trees that are similar enough to be existing pathways known to the system, relative efficiency can, in one embodiment, be accomplished by a simple ranking according to the efficacy criteria established for the system. For instance, this can be represented using a chart where column headings represent grading criteria, in order of importance, and relative efficiency in each category is reported relative to the optimal profile.

Similarly, in a further embodiment of the present invention, caregivers can be rated or ranked using, for instance, the final results of their contribution to tracking a patient through a particular clinical pathway. If a caregiver deviates from the optimal (default) pathway, yet still concludes with sufficiently successful outcome results, then the caregiver would be accorded a more positive rating. Again, ratings are based on the criteria as described above. In this embodiment, a simple ranking of patient data relative to the criteria is generated.

In a further embodiment, the historical database further stores the identity of the medical care provider determining the selection subsequent decision element and wherein the computing means is further responsive to the identity. In an alternate embodiment, the historical database further stores a rating for each of the historical clinical pathways in the database, and wherein the computing means is further responsive to the historical pathway ratings.

II. Data Inputting System Including Stable Acute Care System

The improved input systems of the invention make possible a new type of care, stable acute care. The above data gathering and manipulation systems rely heavily upon access to a database of clinical pathways. Pursuant to the present invention, systems for inputting this information in a format suitable for the purposes described herein are also provided.

Using the present input systems, post-operative surgical procedures having any of following properties may be suitable candidates for stable acute care and prequalification for appropriate (early or late) post-operative hospital discharge. Such patients include those who have been discharged very quickly and are in need of possible IV fluid, IV medication, or nursing care; patients having surgeries where there has been an abdominal incision with significant manipulation of the intestines which would have required a post-operative ileus in the past; and patients where it is desirable to discharge the patient sooner than is standard care (e.g., as recited in Milliman & Robertson) in this country.

Stable acute care is appropriate for a variety of procedures. Stable acute care is made possible using the prequalification and communication systems of the present invention. For instance, using gynecological oncology as an example, radical hysterectomies, procedures with lymph node dissections, debulking procedures, procedures with gastrointestinal anastomoses, and even vaginal procedures may be suitable for stable acute care.

Regardless of the particular procedure being performed, in each case the initial history and physical are evaluated and entered into the system. Any conditions which would restrict a patient from receiving stable acute care are specifically determined for the patient. For instance, such conditions can include, but are not limited to, whether the patient has a 24 hour care giver, whether the patient's environment is inappropriate (for example, the patient has no electricity or no refrigerator), or whether the patient has particular medical problems or physical problems (absolute restrictive criteria would include patient with recent heart attack or a recent CVA). Once a patient is prequalified by the system as an appropriate candidate based on the procedure and the above noted restrictive criteria, the patient is then informed about the program. Assuming consent, the patient may then be seen by a nurse preferably capable of performing stable acute care who will educate them and give them other appropriate information.

After obtaining prequalification information and determining that the patient is suitable for receiving stable acute care, the system develops an appropriate set of orders for the specific surgery or procedure the patient is undergoing. The initial orders correspond to a default clinical pathway and, depending on the procedure, there may be as few as only five or six different default orders per procedure such that the difference between post-operative and/or stable acute care for a radical hysterectomy and a mastectomy may be very minimal.

For use in the system, a questionnaire (again representing the default clinical pathway) is also developed specifically for each procedure. The questionnaire is later processed by the computer software to develop a SOAP note for the patient. When the patient is visited by the nurse, the SOAP note is generated by the computer for that visit and/or procedure. In a similar fashion, events such as IV hydration and IV meds and the use of H2 blockers such as TAGAMET® are also addressed for each procedure. Often, the decision elements or points which yield daily progress notes are similar from one procedure to another. Additionally, an order sheet may be created and may be modified by the physician or the nurse on a daily basis and the orders on the order sheet are determined from the initial order sheet that was created. In this fashion, the initial order sheet is essentially a clinical pathway printout, or at least a decision data element and subsequent data element printout.

In essence, the system creates a universal protocol template and, often, only minor changes are needed for each procedure for a specific plan. The data elements tracked in the model include, but are not required to include and are not limited to, appropriate procedures, restrictive criteria for patients, insurance information, pre-operative education, the clinical pathway, daily order sheets for subsequent orders, the questionnaire developed to determine specific notes, and daily progress sheets created to track the fluids, IV's, or medications given.

The patient information is collected in the doctors office during the first visit. Once the patient is known to be, for instance, an insurance candidate, the patient then receives appropriate information on a pre-operative visit. The patient is educated and given any appropriate information at that time. In the post-operative period in the hospital, once the patient appears to be in satisfactory condition to be released, the nursing care team is contacted and an arrangement is made for visits at the patient's house or other stable acute care facility.

Criteria for discharge may be simple or complex. For instance, the patient for some procedures need only demonstrate adequate pain control and no significant medical or physical problems. As long as the patient is not demonstrating any nausea, vomiting or GI dysfunction, remains afebrile, and does not demonstrate any medical complications, the patient can be released to at least a stable acute care facility. Prior to the patient being released, the default clinical pathway is generated for the patient by the system and is used to instruct the nurse care giver as to how many times a day to see the patient and what kind care to administer to the patient. The nurse practitioner also supplies the appropriate information to the physician and communicates to the physician when a patient is ready to be released from the program.

Questionnaire Language Grammar

The present invention includes data structures used to track clinical pathways. Because the pathways form a decision tree, the decisions at nodes can be analogized to questions. To assist in automating the present system, a special questionnaire language was developed for the system. The grammar and syntax of that system are described in the following paragraphs.

Items are entered into the database in the following form:

(text,{ })[(text,{ }) . . . ]

Notation:

Italics are literal strings.

Items enclosed in square brackets are optional.

Items enclosed in parenthesis are a selection (choose one of the list).

Ellipses indicate that you can repeat the previous grouped item.

Items enclosed in curly braces are format strings for field entry.

Valid Operator List

Following is the list of valid operators:

Numeric

{INT, s[,[n],[m]][:d]}

{FLOAT, x.y[,[n],[m]][:d]}

Text

{CHAR,(s,"(x,9,char)")[:d]}

{RADIO,(h,v)9,"text") . . . [:d]}

{CHECK,(h,v)(,"test") . . . [:d]}

Date/Time

{TODAY}

{NOW}

{DATE,n[:d]}

{TIME,n[:d]}

Boolean
    {BOOL,)n,{ })[:d{ }
    {ERROR}
Valid Operator Description
Numeric
    {INT,s[,[n],[m]][:d]}
Arguments:
    s—size of input field
    n—lower limit,n<=m
    m—upper limit,m>=n
    d—default value
Returns:
    input integer value
Question Example:
    "Enter Pulse:"{INT,4,0,}{IF{ERROR},"Must be greater than 0"{REDO},{NOOP}};
{FLOAT, X.Y[,[n],[m]][:d]}
Arguments:
    x.y—format x—# of digits left of decimal, y—# of digits right of decimal
    n—lower limit,n<=m
    m—upper limit,m>=n
    d—default value
Returns:
    input floating point value
Question Example:
    "Enter CBC count:"{FLOAT,1.2,0.0,5.0}{IF{ERROR}, "Must be between 0 and 5"{REDO},{NOOP}};
Text {CHAR,(s,"(x,9,char)")[:d]}
Arguments:

s—size of input field
    mask, x matches any character, 9 matches numbers, any other character is a literal.
    d—default value
Returns:
    string value of the input
Question Example:
    "Enter SSN:"{CHAR,"999-99-9999"};
    "Enter Name;"{CHAR,40};
(RADIO,(h,v)(,"text") . . . [:d]}
Arguments:
    h,v—horizontal or vertical presentation
    "text"—items to be selected
    d—default item number
Returns:
    integer—corresponds to selected item, beginning with 0
Question Example:
    "Select One:"{RADIO,h,"item 1","item 2","item 3":2};
This would display as:
    Select One:item 1( ),item 2 ( ),item 3 (x)
This would return a 2, if item 1 were selected, item 3 would automatically de-select and the operation would return 0.
{CHECK,(h,v)(,"test") . . . [:d]}
Arguments:
    h,v—horizontal or vertical presentation
    "text"—items to be selected
    d—default item number
Returns:
    array of integers—corresponds to all selected items Question Example:
    "Which of the following do you have:"{CHECK,v, "diabetes", "hypertension","hangnail"};
This would display as:
    Which of the following do you have:
        [ ]Diabetes
        [ ]Hypertension
        [ ]Hangnail
Date/Time
    {TODAY}
Returns:
    integer—Julian number of today's date
{NOW}
Returns:
    integer—integer time since midnight
{DATE,n[:d]}
Arguments:
    n—number of format
    1—mm/dd/yy
    2—dd-mmm-yy
    d—default
Returns:
    integer—Julian number of the date
Question Example:
    "Procedure Schedule time:"{TIME,2};
BOOLEAN
{BOOL,n["d]}
Arguments:
    n—format
    1—yes/no
    2—true/false
    d—default value,) or 1
Returns:
    0 for false/negative
    1 for true/positive
Question Example:
    "All vital signs normal?"{IF({BOOL,1:1}),{DEFAULT, {GROUP}},{NOOP}}
{ERROR}
Returns:
    0 for no errors
    1 for errors exist
Question Example:
    see INT example
Control
{IF(exp),[{1}],{2}]}
Arguments:
    (exp)—boolean expression, accepts<><=>==
Returns:
    {NOOP}
Question Example:
    If exp is true, 1 is performed. If exp is false, 2 is performed. {DEFAULT, (screen id, tab id, group id, question id, field id)[, (screen id, tab id, group id, question id, field id]. . . }
Arguments
    5 tuple that specifies questions to trip default value on.
Returns:
    {NOOP}
{ANSWER}
Returns:
    Text of entire question after answer accepted
{NOOP}
Null operation.

{ERRMSG, TEXT}
Arguments:
    test—Text to display in error status box.
Question Example:
    See INT example
{SCREEN}
Returns:
    Current screen id
{TAB}
Returns:
    Current tab id
{GROUP}
Returns:
    Current group id
{QUESTION}
Returns:
    Current question id
{FIELD}
Returns:
    Current field id With reference to FIGS. 1A–1B, a sample daily routine for a caregiver using the system of the present invention is depicted. For purposes of FIG. 1A, it will be assumed that the caregiver is a nurse or other medical professional who provides the care to a patient in the home, or other location remote from a primary care center (e.g., hospital, doctor's office, etc.). Of course, other suitable applications of the present invention may also be made, and the patient need not necessarily be in the home, but may also be in other locations (even in the hospital). Also, for purposes of the present discussion, it will be assumed that a client computer 401 (see FIG. 4) may be used by either a nurse or by a physician. The mode of operation may be dictated by who logs into the particular computer 401. Of course, in another embodiment, two separate types of client computers 401 could also be created, one for a physician and one for a nurse, etc.

In step 101, a nurse logs into a client computer 401. In step 102, the nurse, using the client computer 401 (FIG. 4) communicates with the server 402, in order to obtain updated pathway instructions, etc., regarding what steps to perform during visit(s) for one or more patient(s). The communication can take place via modem and standard phone lines, via wireless transmission (e.g., cellular, etc.), via the Internet, or via any other communication link.

In steps 103–104, the nurse prepares for the visit to the patient (or a first patient, if more than one) by obtaining the necessary supplies, etc., and travels to the patient's location. In step 105, the nurse, through client computer 401, may again communicate with server 402, in order to obtain the most current instructions and data.

In step 106 and 108, the client computer 401, via the questionnaire language previously described, or through any other data collection mechanism, may obtain data from the nurse or other source corresponding to the clinical pathway to be followed, as dictated by the physician. As a result, SOAP notes may be generated, alerts can be generated, etc., for ultimate retransmission to the server 402.

Alternatively, or in addition, in step 107 the nurse may carry out orders created by the physician and transmitted in steps 102 and/or 105 from the server 402 to the client computer 401. The results of such orders may generate a flow of care to be followed by the nurse, and/or may generate alerts, etc. In step 109, the nurse records in the client computer 401 compliance or non-compliance with the orders. If non-compliance, the reasons are also stored. gain, all such stored data may later be transmitted back to the server 402.

In step 110, the client computer 401 communicates with the server 402, in order to update both the computer 401 and server 402 as in steps 102 and 105. In step 111, if there are additional patients assigned to the nurse, as would be indicated on a list maintained on the computer 401 (as communicated from the server 402), then steps 104–110 may be repeated for each of the remaining patients. After all patients have been processed by the nurse, the final step 112 is reached.

Figure 1B:
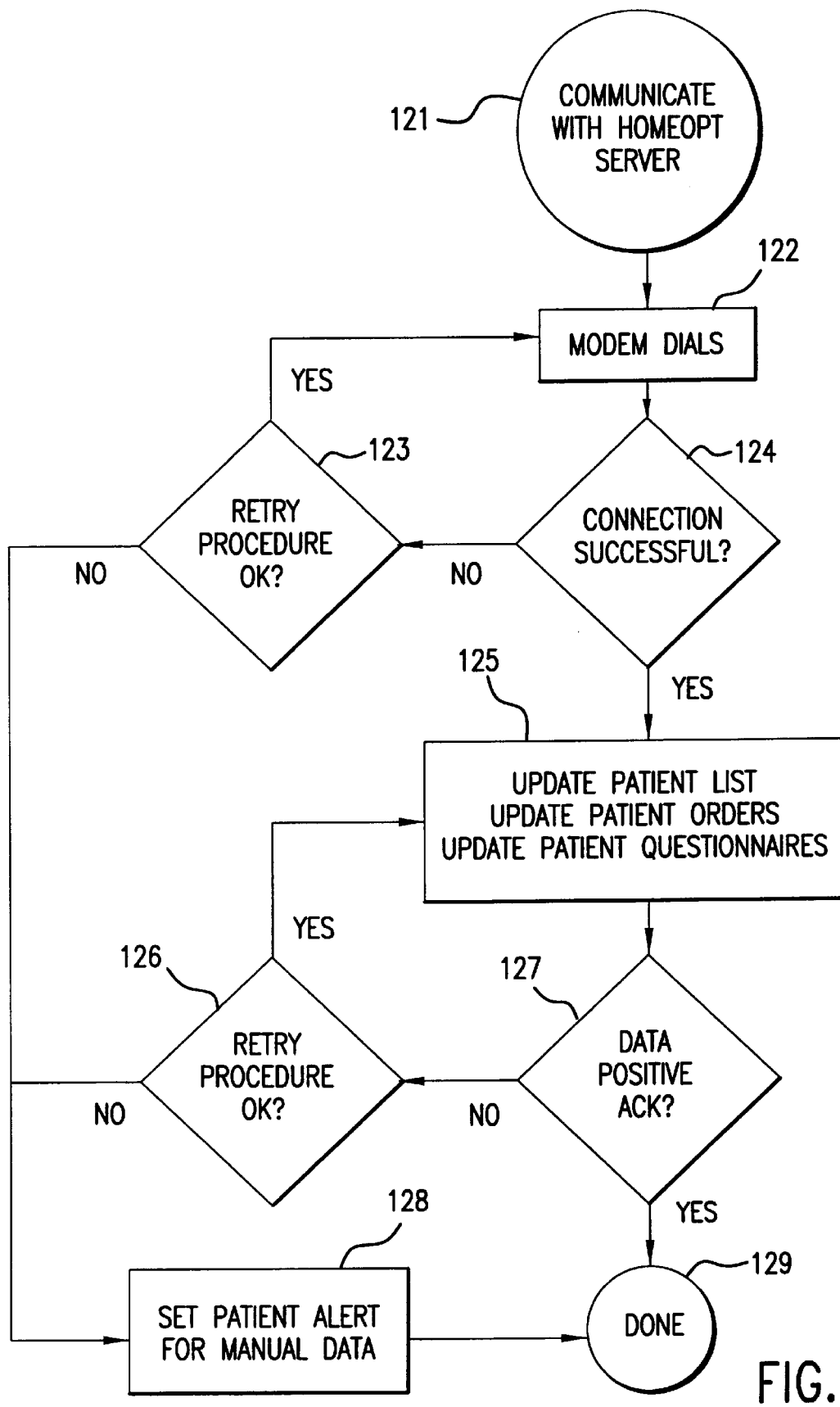

Steps 102, 105 and 110, wherein the client computer 401 communicates with the server 402, are each described in further detail in steps 121–129, depicted in FIG. 1B. In step 121, the processes commences. In step 122, the modem on the client computer 401 dials into the server 402. Again, this assumes that the computer 401 and server 402 are to be connected via modem and standard telephone lines. Again, it will be understood that this connection may be accomplished in a variety of ways, including over telephone lines, via a wireless connection (cellular or otherwise), via the Internet, etc. For purposes of the present discussion, a modem and telephone line connection will be assumed.

In step 124, if the modem connection was not successful, then in step 123 the user may be allowed to try the connection again, returning to step 122. If another attempt is not to be made, then step 128 is encountered, as described further below.

Assuming the connection between the client computer 401 and server 402 is successful in step 124, then in step 125 the patient list, patient orders and patient questionnaire is updated. Specifically, the client computer 401 sends information to the server 402 regarding the actions that the nurse has taken (as input into the client computer 401 by the nurse), and the server 402 sends to the client computer 401 the updated patient list, patient orders, patient questionnaires, flow of care, etc. Other data as appropriate may also be transmitted back and forth between the client computer 401 and the server 402.

In step 127, if the data has been correctly exchanged between the client computer 401 and server 402, then final step 129 is encountered. Otherwise, step 126 is encountered, where a decision is made whether to retry the transmission. If a retry is to be attempted, then step 125 is performed again. Otherwise, step 128 is encountered. In step 128, an alert is set at the client computer 401, indicating that the transmission between the client computer 401 and server 402 was unsuccessful, allowing the nurse to manually provide the data to the physician, or other personnel at the central location (e.g., via voice telephone, etc.).

Figure 2A:
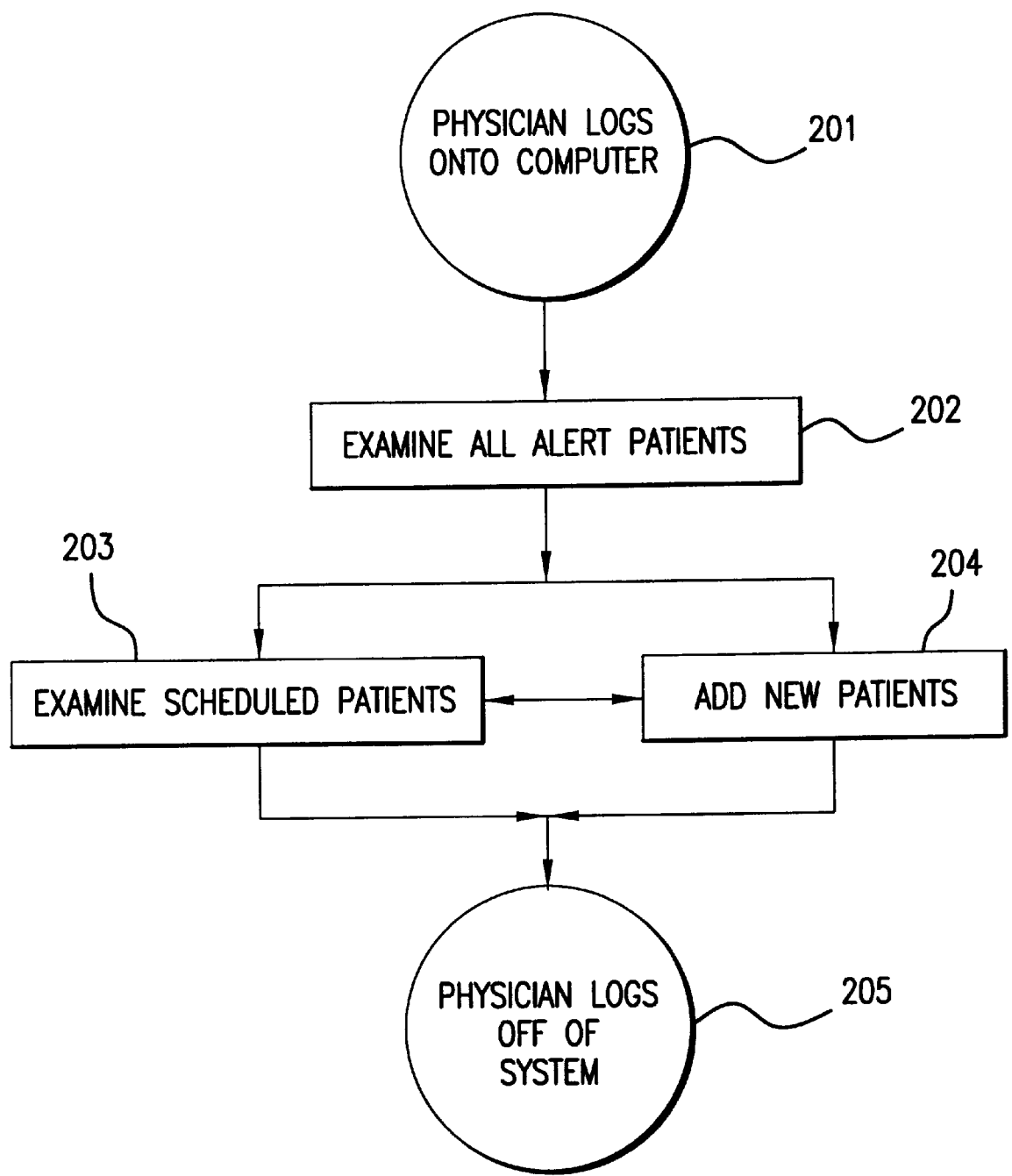
FIGS. 2A, 2B, and 2C show flowcharts of the questionnaire system in operation from the physician's point of view.
Figure 2B:
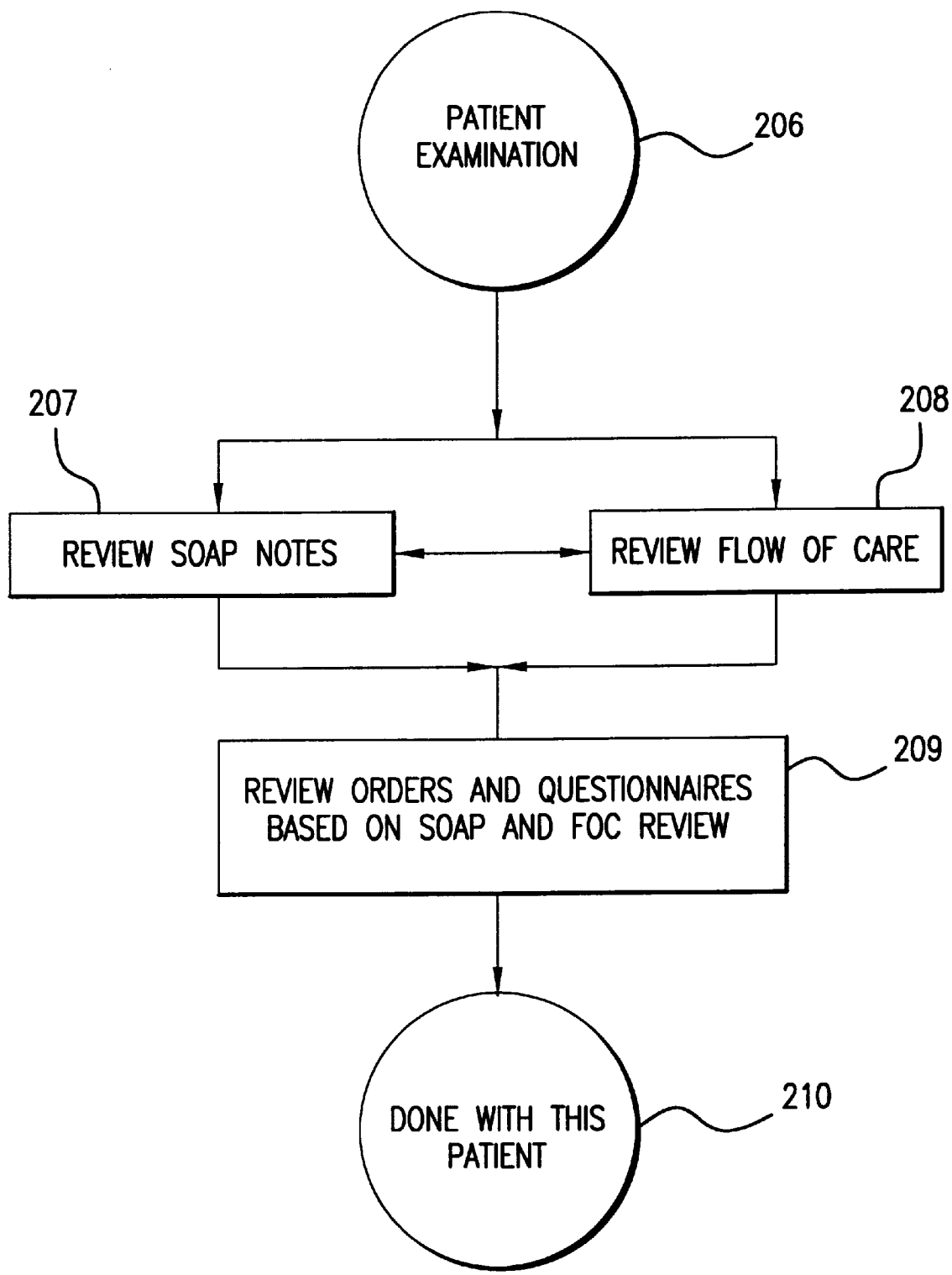
Figure 2C:
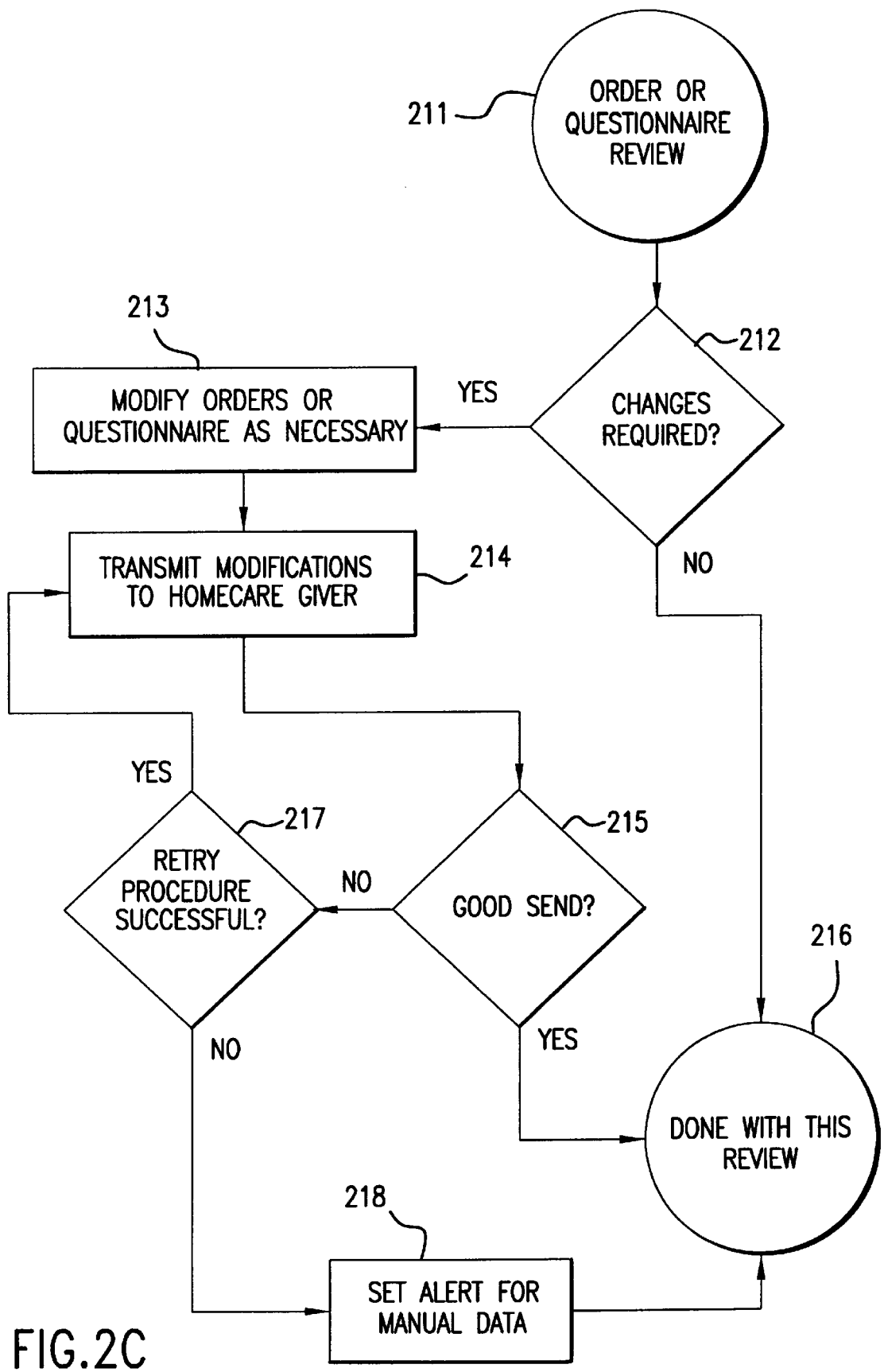

Just as FIGS. 1A and 1B depict a remote caregiver's routine, FIGS. 2A–2C depict a sample routine performed by a physician. With reference to FIG. 2A, in step 201, the physician logs into a client computer 401. In step 202, the physician may examine all patients for whom an alert has been generated (such as in certain of the steps of FIGS. 1A and 1B, described previously). The physician may thereafter selectively examine previously scheduled patients (step 203) and/or add new patients to be examined (step 204). At some point thereafter, the physician may log off of the client computer 401 in step 205.

FIG. 2B depicts the patient examination step 203 of FIG. 2A in further detail. In step 206, the examination process begins. Using the client computer 401, the physician may selectively review SOAP notes generated for the patient (step 207) and/or review the flow of care (FOC) generated for the patient (step 208). In step 209, the physician may review orders and questionnairse based on the SOAP notes and flow of care. Finally, in step 210, the physician is done with the present patient.

Step 209 of FIG. 2B is described in further detail with respect to FIG. 2C. In step 211, the review of order or questionnaire process begins. In step 212, the physician determines whether changes are required in the patient's flow of care, or in the questionnaire(s) to be used by the nurse. If changes are required, then the physician may modify the orders or the questionnaire as necessary in step 213. In step 214, such modifications are transmitted to the nurse's computer 401 using the process previously described with respect to FIG. 1B. In step 215, if the transmission is successful, then step 216 is finally encountered. If not, then in step 217 a decision is made whether to retry the transmission. If so, step 214 is encountered again. Otherwise, an alert is set in step 218, and step 216 is finally encountered.

Figure 3A:
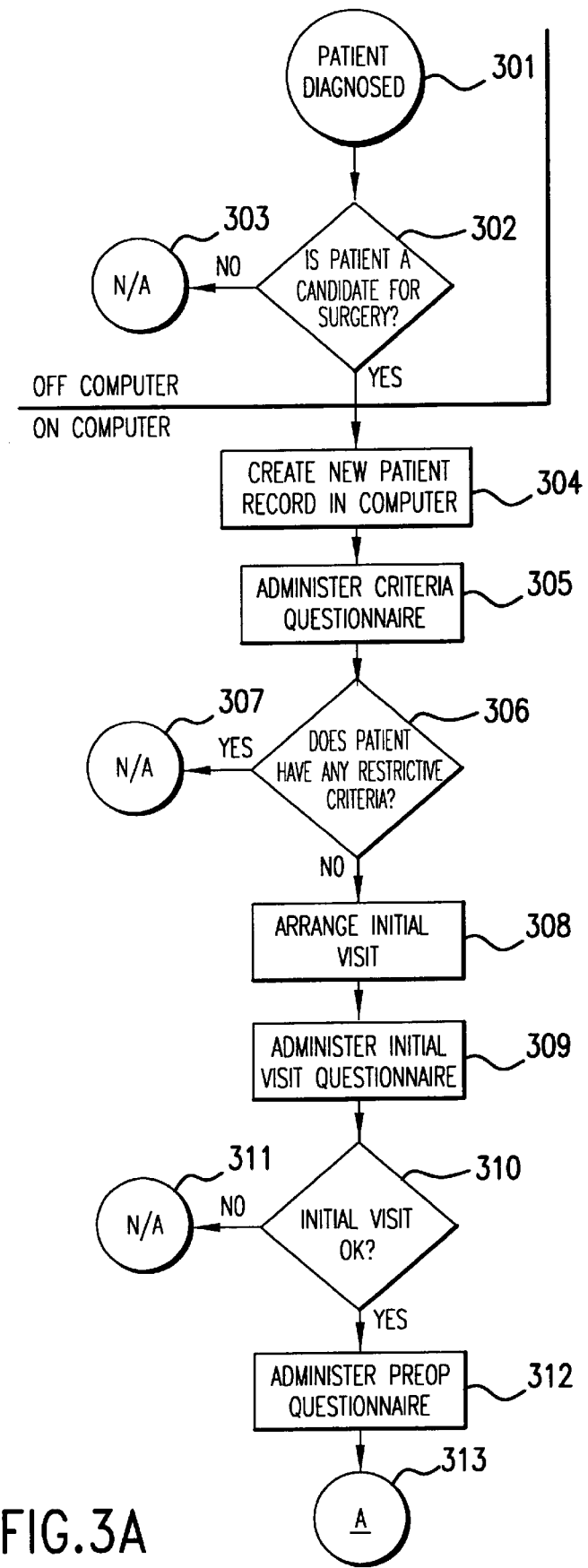
FIGS. 3A and 3B show flowcharts detailing the steps taken to add a patient to the system.
Figure 3B:
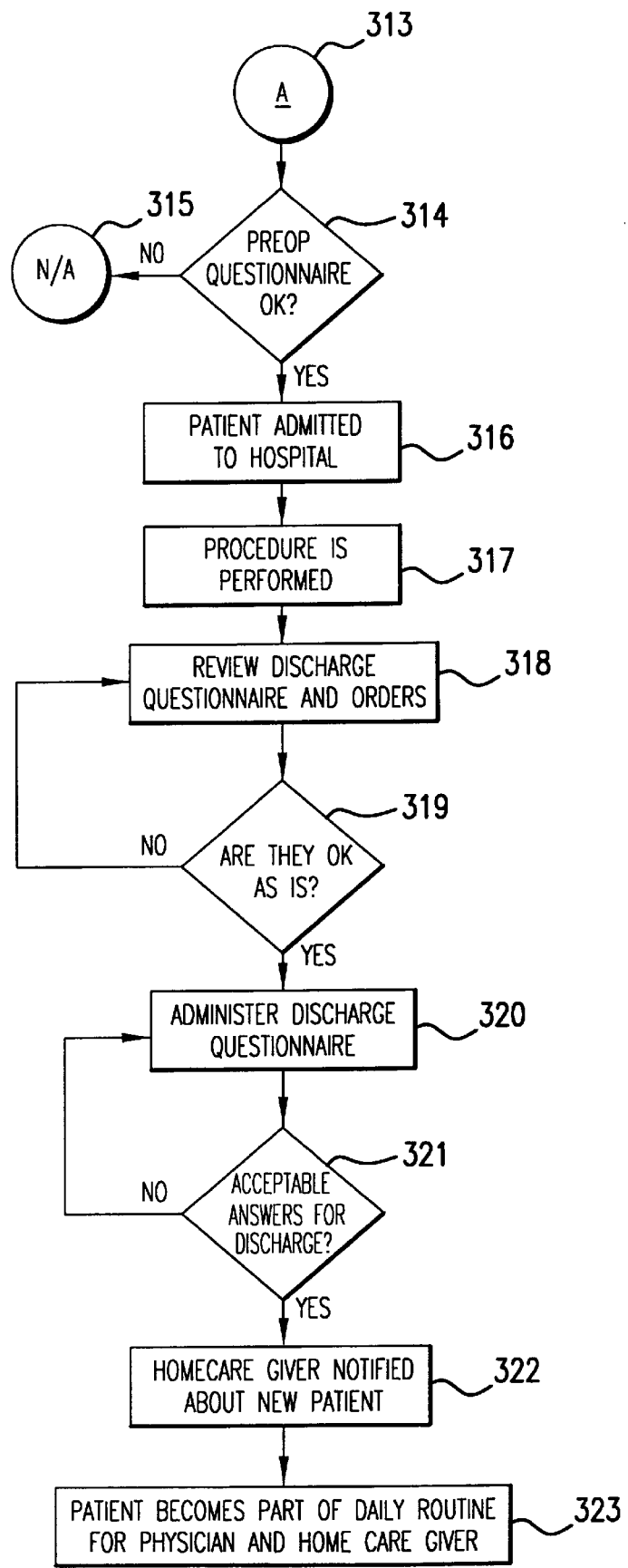

FIGS. 3A and 3B depict in further detail the new patient addition step 204 of FIG. 2A. In step 301, the process begins, and the patient is diagnosed with a particular ailment by a physician, etc. In step 302, a decision is made whether the patient is a candidate for a particular type of surgery, for example. If not, then step 303 is encountered, indicating that the process of FIGS. 3A and 3B is not necessarily applicable.

In step 304, a new patient record is created, using for example the client computer 401 and the server 402. This record may be stored on the server 402, or at any other external location. In step 305, a criteria questionnaire is administered on the client computer 401, in order to determine whether the patient satisfies the criteria to be eligible for, for example, home health care. Examples of such criteria and conditions have been previously described elsewhere.

In step 306, a decision is made whether the patient has any restrictive criteria, which would prevent the patient from being eligible for home health care. If so, then step 307 is encountered, and the process stops. Otherwise, in step 306 an initial visit is arranged. In step 309, an initial visit questionnaire is administered, and in step 310 a determination is made whether the initial visit is OK. Of not, then step 311 is encountered.

Otherwise, in step 312, a preop questionnaire is administered, and step 313 is encountered. In step 314, a determination is made whether the preop questionnaire is OK. If not, step 315 is encountered. Otherwise, in step 316 the patient is admitted to the hospital, and in step 317 the procedure is performed. In steps 318–319, a discharge questionnaire and orders are reviewed until OK, and in steps 320–321 the discharge questionnaire is administered until acceptable answers are obtained. In step 322, the home care provider is notified regarding the new patient, and in step 323 the patient becomes part of the daily routine of the physician and home care provider, previously described.

The present invention provides for a very flexible data structure to be used for collecting data, as well as a relatively detailed amount of information to be collected about patients and their progress through a clinical pathway. This data format is required for purposes of optimizing the pathways and procedures, as previously described. Because of the flexible data structure allowed by the present invention, the present invention has the ability to produce custom reports. These reports can easily be tailored to present information in any format desired. Examples of this might be productions of the standard "Home Health Certification and Plan of Care" form HCFA-485 and the HCFA-487 form, which is an addendum to the plan of treatment or a medical update.

Both of these forms can be constructed from a subset of the data required by the present invention. Home health agencies, Medicare and many private insurance plans use the HCFA-485 form for reimbursement of services. Changes to orders and the patient's condition are reported on the HCFA-487 form. Both of these forms are used to track a patient's progress through some treatment plan. Within the present invention, this treatment plan corresponds to a clinical pathway. Progress may be noted in the present invention by recording visits to the patient, and the patient's actual condition. Changes made to orders are recorded as changes to the pathway. As a result of recording the information needed by the system of the present invention, it would be easy to produce reports, in whatever format needed, to demonstrate compliance with various regulatory or insurance requirements.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method for manipulation and analysis of data related to clinical pathways, the method comprising the steps of:

(a) providing a clinical pathway database for storing:
  (i) an initial procedure decision data element, corresponding to a decision point within the clinical pathway; and
  (ii) at least one subsequent decision data element, corresponding to an available subsequent decision point within the clinical pathway;
  (iii) a patient identification data element corresponding to the initial and subsequent decision data elements for a particular patient;
  (iv) at least one patient visit data element corresponding to the patient identification data element; and
  (v) a time stamp data element corresponding to each of the at least one patient visit data elements:

(b) providing a historical clinical pathway database for storing previously selected subsequent decision data elements, selected corresponding to the initial procedure decision data element;

(c) selecting one of the at least one subsequent decision data elements stored within the clinical pathway database;

(d) comparing the selected subsequent decision data element, including the associated patient identification data element, patient visit data element and time stamp data element, with the previously selected subsequent decision data elements, including the associated patient identification data element, patient visit data element and time stamp data element, stored in the historical clinical pathway database; and (e) based upon predetermined correlation criteria between the selected subsequent decision data element and the previously selected subsequent decision data elements stored in the historical clinical pathway database, modifying the at least one subsequent decision data element within the clinical pathway database.

2. A system for manipulation and analysis of data related to clinical pathways, comprising:

(a) a clinical pathway database for storing:
  (i) an initial procedure decision data element, corresponding to a decision point within the clinical pathway;

(ii) at least one subsequent decision data element, corresponding to an available subsequent decision point within the clinical pathway;

(iii) a patient identification data element corresponding to the initial and subsequent decision data elements for a particular patient;

(iv) at least one patient visit data element corresponding to the patient identification data element; and (v) a time stamp data element corresponding to each of the at least one patient visit data elements;

(b) a historical clinical pathway database for storing previously selected subsequent decision data elements, selected corresponding to the initial procedure decision data element; and (c) processing means, including a storage device, for performing the steps of:

(i) selecting one of the at least one subsequent decision data elements stored within the clinical pathway database;

(ii) comparing the selected subsequent decision data element, including the associated patient identification data element, patient visit data element and time stamp data element, with the previously selected subsequent decision data elements, including the associated patient identification data element, patient visit data element and time stamp data element, stored in the historical clinical pathway database; and (iii) based upon predetermined correlation criteria between the selected subsequent decision data element and the previously selected subsequent decision data elements stored in the historical clinical pathway database, modifying the at least one subsequent decision data element within the clinical pathway database.

* * * * *